United States Patent
Yu

(10) Patent No.: US 10,556,016 B2
(45) Date of Patent: Feb. 11, 2020

(54) ARTIFICIAL ANTIGEN-PRESENTING CELLS AND METHODS FOR PRODUCING AND USING THE SAME

(71) Applicant: Indiana University Research and Technology Corporation, Indianapolis, IN (US)

(72) Inventor: Yan Yu, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 251 days.

(21) Appl. No.: 15/513,143

(22) PCT Filed: Sep. 23, 2015

(86) PCT No.: PCT/US2015/051756
§ 371 (c)(1),
(2) Date: Mar. 21, 2017

(87) PCT Pub. No.: WO2016/049210
PCT Pub. Date: Mar. 31, 2016

(65) Prior Publication Data
US 2017/0304462 A1    Oct. 26, 2017

Related U.S. Application Data

(60) Provisional application No. 62/054,831, filed on Sep. 24, 2014.

(51) Int. Cl.
| | | |
|---|---|---|
| A61K 38/00 | (2006.01) | |
| A61K 45/00 | (2006.01) | |
| A61K 47/68 | (2017.01) | |
| A61B 5/16 | (2006.01) | |
| A61B 5/00 | (2006.01) | |

(52) U.S. Cl.
CPC .......... *A61K 47/6811* (2017.08); *A61B 5/165* (2013.01); *A61B 5/167* (2013.01); *A61B 5/4076* (2013.01); *A61B 5/00* (2013.01)

(58) Field of Classification Search
None
See application file for complete search history.

(56) References Cited

U.S. PATENT DOCUMENTS

| | | |
|---|---|---|
| 2010/0330345 A1 | 12/2010 | Mirkin et al. |
| 2011/0250427 A1 | 10/2011 | Kotov et al. |
| 2014/0248210 A1 | 9/2014 | Bradbury et al. |

FOREIGN PATENT DOCUMENTS

| | | |
|---|---|---|
| WO | WO2006/073773 A2 | 7/2006 |
| WO | WO2013/086500 A1 | 6/2013 |
| WO | WO2013/116473 A1 | 8/2013 |

OTHER PUBLICATIONS

Bo Chen et al ( ACS Applied Materials and Method, 2014, ,v.6 pp. 18435-18439.*
International Search Report and Written Opinion issued by the ISA/US, Commissioner for Patents, dated Feb. 1, 2016, for International Application No. PCT/US2015/051756; 23 pages.
Sunshine, Joel C., and Green, Jordan J., "Nanoengineering Approaches to the Design of Artificial Antigen-Presenting Cells." *Nanomedicine* (London, England) vol. 8, No. 7 (Jul. 1, 2013); pp. 1173-1189; available from the Internet at https://www.ncbi.nlm.nih.gov/pmc/articles/PMC3951141/pdf/nihms558407.pdf.

* cited by examiner

*Primary Examiner* — Michail A Belyavskyi
(74) *Attorney, Agent, or Firm* — Faegre Baker Daniels LLP

(57) ABSTRACT

Described herein are biomimetic Janus particles useful as artificial antigen presenting cells capable of activating T cells in vitro. "Bull's eye" ligand patterns mimicking either the native or reverse organization of the T cell immunological synapse are provided on the surface of nano- or micro-sized particles. Methods for activating T cells in vitro using biomimetic Janus particles described herein are also provided. T cells activated by the biomimetic Janus particles can be used in adoptive immunotherapies for treating cancer, tolerance induction in autoimmune disease, autologous immune enhancement therapy, and viral infection immunotherapy. Also described herein are methods for producing a biomimetic Janus particle.

31 Claims, 8 Drawing Sheets

ARTIFICIAL ANTIGEN-PRESENTING CELLS AND METHODS FOR PRODUCING AND USING THE SAME

CROSS-REFERENCE TO RELATED APPLICATIONS

This application is a U.S. National Stage Application of International Patent Application No. PCT/US2015/051756, filed Sep. 23, 2015, which claims the benefit of U.S. Provisional Application No. 62/054,831, filed on Sep. 24, 2014, each of which is expressly incorporated herein by reference in its entirety.

STATEMENT REGARDING FEDERALLY SPONSORED RESEARCH

This invention was not made with government support.

BACKGROUND

T cells, as the key player in cell-mediated immunity, can be harnessed to fight against cancer, induce tolerance in autoimmune disease, enhance immune therapy, and to fight against viral infection. An essential step in employing T cells for use these therapies, is to stimulate T cell activation in vitro. T cells in vivo are stimulated by antigen-presenting cells (APCs), such as dendritic cells. However, isolation of native APCs for T cell-based immunotherapy is not only time-consuming and expensive, but also difficult to reproduce. To overcome those challenges, synthetic particles that display well-defined antigens and co-stimulatory ligands have been developed as artificial APCs to provide more consistent stimulation of T cells in vitro. A large spectrum of particles has been designed to mimic different aspects of the native APCs, including size, shape, ligand mobility, and multivalency. However, these particles are generally randomly coated with proteins, and do not truly mimic the native immunological synapse.

SUMMARY

Described herein are biomimetic Janus particles useful as artificial antigen presenting cells capable of activating T cells in vitro. "Bull's eye" ligand patterns mimicking either the native or reverse organization of the T cell immunological synapse are provided on the surface of nano- or micro-sized particles. Methods for activating T cells in vitro using biomimetic Janus particles described herein are also provided. T cells activated by the biomimetic Janus particles can be used in adoptive immunotherapies for treating cancer, tolerance induction in autoimmune disease, autologous immune enhancement therapy, and viral infection immunotherapy. Also described herein are methods for producing a biomimetic Janus particle.

In a particular embodiment provided herein is a biomimetic Janus particle comprising a particle, at least one substantially concentric pattern of a first ligand population bound to the particle, wherein the first ligand population comprises one or more ligands involved in T cell activation and/or one or more molecules to which a ligand involved in T cell activation may be bound, and a second ligand population bound to the particle, wherein the second ligand population is different than the first ligand population and does not substantially overlap the substantially concentric pattern of the first ligand population, and wherein the second ligand population comprises one or more ligands involved in T cell activation and/or one or more molecules to which a ligand involved in T cell activation may be bound, wherein one of the first ligand population or second ligand population comprise an integrin-binding ligand.

In another particular embodiment provided herein is a method for producing a biomimetic Janus particle, the method comprising the steps of a) forming at least one substantially concentric pattern of a first ligand population on at least one particle, wherein the first ligand population comprises one or more ligands involved in T cell activation and/or one or more molecules to which a ligand involved in T cell activation may be bound, and b) incubating the at least one particle following completion of step a) with a second ligand population, wherein the second ligand population is different than the first ligand population and does not substantially overlap the substantially concentric pattern of the first ligand population, and wherein the second ligand population comprises one or more ligands involved in T cell activation and/or one or more molecules to which a ligand involved in T cell activation may be bound. The method for forming the at least one substantially concentric pattern of the first ligand population on the at least one particle can be any form of nano- or microlithography, including but not limited to microcontact printing, photolithography, electron beam lithography, nanoimprint lithography, interference lithography, X-ray lithography, extreme ultraviolet lithography, magnetolithography, and dip-pen lithography.

In embodiments using microcontact printing to form the at least one substantially concentric pattern of the first ligand population on the at least one particle, the method comprises the steps of a) forming a monolayer of particles on a substrate, b) providing a section of cured polymer, c) incubating a surface of the section of cured polymer with a first ligand population, wherein the first ligand population comprises one or more ligands involved in T cell activation and/or one or more molecules to which a ligand involved in T cell activation may be bound. d) drying the cured section of polymer incubated with the first ligand population, e) embedding the monolayer of particles in the dried, cured section of polymer incubated with the first ligand population by pressing the dried, cured section of polymer incubated with the first ligand population against the monolayer of particles, f) removing the particles from the substrate, wherein the particles either remain embedded in, or are released from, the dried, cured section of polymer incubated with the first ligand, and g) incubating the particles with a second ligand population, wherein the second ligand population comprises one or more ligands involved in T cell activation and/or one or more molecules to which a ligand involved in T cell activation may be bound.

In embodiments wherein the particles remain embedded in the dried, cured section of polymer incubated with the first ligand population, the method further comprises a step of releasing the particles from the dried, cured section of polymer incubated with the first ligand population following the incubation with the second ligand population, so as to reveal a substantially concentric pattern of the first ligand population formed on the particle substantially surrounded by the second ligand population. In certain embodiments, the released particles are re-incubated with the second ligand population.

In embodiments wherein the particles are released from the dried, cured section of polymer incubated with the first ligand population, wherein steps a) through f) are repeated with the particles one or more times before completing step g), so as to produce two or more substantially concentric patterns of the first ligand population formed on the particle substantially surrounded by the second ligand population.

The substrate used for formation of the monolayer can be any substrate suitable for particle monolayer formation. In one embodiment, the substrate is glass, and more specifically, a glass microscope slide. In certain embodiments, the substrate is cleaned prior to the formation of the monolayer of particles thereon. The substrate can be cleaned with a solvent to remove organic residues and to hydroxylate the surface of the substrate, making it hydrophilic. In one embodiment, the solvent used to clean the substrate is piranha solution comprising $H_2SO_4/H_2O_2$. In another embodiment, the substrate is cleaned at an elevated temperature of 5° C. for about 15 minutes. Following cleaning, the substrate is generally rinsed. In one embodiment, the substrate is rinsed in ultrapure water following cleaning.

In certain aspects, the particles are cleaned prior to forming the monolayer of particles on the substrate. In one aspect, the particles are cleaned using piranha solution comprising $H_2SO_4/H_2O_2$. Formation of the monolayer of particles on the substrate is, in certain embodiments, accomplished via solvent evaporation or dip coating.

In certain embodiments described herein, the cured polymer is a silicon-based organic polymer, such as polydimethylsiloxane. The cured polymer has an area sufficient to contact the microlayer of particles on the substrate, and is generally about 0.5 cm$^2$ to about 10 cm$^2$. In certain aspects, the surface of the cured polymer is treated to make its surface hydrophilic. This provides for improved adsorption of the first ligand population to the cured polymer. In certain aspects, this is achieved by treating the cured polymer with $H_2SO_4/H_2O_2$. The dried, cured section of polymer incubated with the first ligand population is pressed against the monolayer of particles immediately following drying. In certain aspects, the dried, cured section of polymer incubated with the first ligand population is pressed against the monolayer of particles at a pressure of about $0.5\times10^4$ to about $2.5\times10^4$ Pa. In a particular embodiment, the dried, cured section of polymer incubated with the first ligand population is pressed against the monolayer of particles at a pressure of about $1.5\times10^4$ Pa. The dried, cured section of polymer incubated with the first ligand population is pressed against the monolayer of particles for about 30 seconds to about 10 minutes. The diameter of first ligand population deposited on the particle is directly related to the pressure applied to the cured section of polymer incubated with the first ligand population when pressed against the monolayer of particles.

In other embodiments, the particles embedded in the dried, cured section of polymer incubated with the first ligand population are incubated in the second ligand population for about 0.5 to about 3 hours. In a particular embodiment, the particles embedded in the dried, cured section of polymer incubated with the first ligand population are incubated in the second ligand population for about 1.5 hours.

In another particular embodiment provided herein is a method for producing a biomimetic Janus particle using block copolymer self-assembly. Generally, the method comprises the steps of a) providing a first block copolymer to which is bound a first ligand population, wherein the first ligand population comprises one or more ligands involved in T cell activation and/or one or more molecules to which a ligand involved in T cell activation may be bound, b) providing a second block copolymer, and c) combining the first block copolymer to which is bound the first ligand population with the second block copolymer, wherein the first block copolymer to which is bound the first ligand and the second block copolymer self-assemble to form at least one substantially spherical biomimetic Janus particle having at least one substantially concentric pattern of the first block copolymer to which is bound the first ligand population. In certain aspects, the bock copolymers undergo directed self-assembly.

In certain embodiments, a second ligand population is bound to the second block copolymer prior to completing the combining step. In other embodiments, the at least one substantially spherical biomimetic Janus particle is incubated with a second ligand population.

Particles described herein can be microparticles or nanoparticles. In certain embodiments, the particle is selected from the group consisting of: a silica particle; a polystyrene particle; a melamine resin particle; and a polymethacrylate particle. In a particular aspect, the particle is a silica particle. The particles have a diameter within the range of about 0.1 μm to about 20 μm. In a particular aspect, the particles have a diameter of about 3 μm.

The at least one substantially concentric pattern of the first ligand population has a diameter within the range of about 10 nm to about 5 μm. In one particular aspect, the at least one substantially concentric pattern of the first ligand population has a diameter within the range of about 1.7 μm.

In certain embodiments described herein, the one or more ligands involved in T cell activation is selected from the group consisting of: anti-CD3 antibody; anti-CD28 antibody; anti-TCR antibody; anti-CTLA4 antibody; and a ligand comprising a general integrin-binding motif, and the one or more molecules to which a ligand involved in T cell activation may be bound is biotin. In a particular aspect, the first ligand population comprises one or more ligands comprising a general integrin-binding motif and the second ligand population comprises one or more ligands capable of binding to at least one component of a T cell TCR complex, forming a reverse bull's eye pattern. In another particular aspect, the first ligand population comprises one or more ligands capable of binding to at least one component of a T cell TCR complex and the second ligand population comprises one or more ligands comprising a general integrin-binding motif, forming a native bull's eye pattern. The ligand comprising a general integrin-binding motif is selected from the group consisting of: fibronectin; collagen; laminin; vitronectin; fibrinogen; and thrombospondin.

In embodiments comprising biotin as one of the ligands, the biomimetic Janus particle or method further comprises one or more streptavidin-conjugated ligands and/or biotinylated ligands capable of binding to at least one component of a T cell TCR complex, wherein the one or more streptavidin-conjugated ligands is bound to the biotin.

In certain embodiments, the one or more ligands capable of binding to at least one component of a T cell TCR complex is selected from the group consisting of: anti-CD3 antibody; anti-CD28 antibody; anti-TCR antibody; and anti-CTLA4 antibody.

In other particular embodiments provided herein, are biomimetic Janus particles produced by a method described herein. In yet other embodiments provided herein are compounds comprising a biomimetic Janus particle described herein.

In another particular aspect provided herein, is a method of activating a population of T cells in vitro, comprising applying one or more biomimetic Janus particles described herein to a population of T cells. The population of T cells can be autologous T cells, isolated from a subject in need of an immunotherapy, heterologous T cells derived from a source other than the subject in need of an immunotherapy, or a combination thereof. The population of T cells can comprise naïve T cell, CD8+ T cells, CD4+ T cells, or a combination thereof. In other embodiments, the population of T cells comprises antigen-specific T cells. In yet other embodiments, the population of T cells comprises tumor antigen-specific T cells.

In certain embodiments, the one or more biomimetic Janus particles are incubated with the population of T cells for about 5 minutes to about 2 week. In a particular aspect, the one or more biomimetic Janus particles are incubated with the population of T cells for about 1 hour to about 60 hours. In another particular aspect, the one or more biomimetic Janus particles are incubated with the population of T cells for about 24 hours to about 48 hours.

In yet another particular aspect provided herein, is a method of administering an immunotherapy to a subject in need thereof, the method comprising administering T cells activated by a biomimetic Janus particle described herein to the subject. The immunotherapy is selected from the group consisting of: adoptive immunotherapy for cancer; tolerance induction in autoimmune disease; autologous immune enhancement therapy; and viral infection immunotherapy. In certain embodiments, the method of administering an immunotherapy to a subject in need thereof further comprises a step of preparative lymphodepletion in the subject prior to administering the activated T cells to the subject.

BRIEF DESCRIPTION OF THE DRAWINGS

FIG. 1A: Schematic representation of ligand-bound T cell receptors (TCRs) and integrins forming "bull's eye" concentric microdomains in the membrane junction, known as the immunological synapse, between a T cell and an antigen-presenting cell. FIG. 1B: Schematic representation of patterns of anti-CD3 and fibronectin on Janus particles resembling the native or reverse "bull's eye" pattern.

FIGS. 3A and 3C: Normalized fluorescence intensities of two representative cells are plotted as a function of time to show the fluctuation of $[Ca^{2+}]$ during T cell activation. Time zero was defined as the time of each cell landing on the bottom of imaging chambers. White arrows indicate Janus particles that were in contact with cells. Anti-CD3 and fibronectin were shown in red and green, respectively, in both images. The global calcium response of T cells stimulated by (FIG. 3B) the reverse (n=96) and (FIG. 3D) the native "bull's eye" Janus particles (n=111) are plotted on a color scale and sorted based upon the fluorescence intensity of the first peak. Scale bars: 5 µm.

DETAILED DESCRIPTION

Figure 1A:
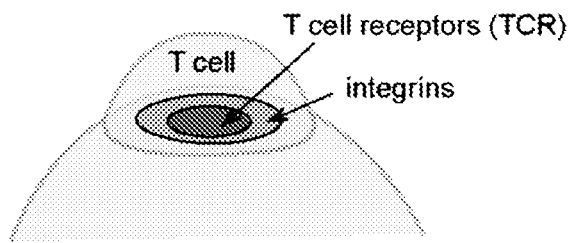
FIGS. 1A-1B: "Bull's eye" Janus particles resemble protein patterns in the immunological synapse.

Throughout this disclosure, various publications, patents and published patent specifications are referenced. The disclosures of these publications, patents and published patent specifications are hereby incorporated by reference into the present disclosure to more fully describe the state of the art to which this invention pertains.

Described herein are biomimetic Janus particles useful as artificial antigen presenting cells capable of activating T cells in vitro. "Bull's eye" ligand patterns mimicking either the native or reverse organization of the T cell immunological synapse are provided on the surface of nano- or micro-sized particles. Methods for activating T cells in vitro using biomimetic Janus particles described herein are also provided. T cells activated by the biomimetic Janus particles can be used in adoptive immunotherapies for treating cancer, tolerance induction in autoimmune disease, autologous immune enhancement therapy, and viral infection immunotherapy. Also described herein are methods for producing a biomimetic Janus particle.

Definitions

In describing the present invention, the following terms will be employed, and are intended to be defined as indicated below.

As used herein, the term "biomimetic" refers to artificially mimicking a natural molecule, compound, or particle. A biomimetic particle described herein has substantially similar T cell activating abilities as a native antigen presenting cell. In a particular embodiment, a biomimetic particle comprises first and second ligand populations. The ligand populations comprise one or more ligands involved in T cell activation, one or more molecules to which a ligand involved in T cell activation may be bound, or a combination thereof. Generally, the first ligand population will be different than the second ligand population. In certain aspects both the first and second ligand populations can comprise of one or more of the same ligands, but will differ in at least one ligand.

The term "ligand" generally refers to a substance, including a protein, that forms a complex that binds specifically and reversibly to another chemical entity to form a larger complex. As used herein, a ligand is usually a signal-triggering molecule, binding to a site on a target protein. As described herein, ligands include any antibody or other ligand capable of binding to a T cell target protein involved in T cell activation or signaling. Ligands may include, but are not limited to, anti-CD3 antibodies, anti-CD28 antibodies, anti-T cell receptor antibodies, ligands comprising a general integrin-binding motif, and biotin. Ligands comprising a general integrin-binding motif generally comprise an arginine-glycine-aspartic acid (RGD) motif, although may comprise a different integrin-binding motif. Ligands comprising a general integrin-binding motif include, but are not limited to, fibronectin, collagen, laminin, vitronectin, fibrinogen, and thrombospondin. "Ligand population" refers to a group of ligands. A ligand population can consist of a single type of ligand, or may comprise several types of ligands. For example, a ligand population may comprise one or more unique anti-CD3 antibodies, each anti-CD3 antibody in the ligand population capable of interacting with one or more CD3 subunits.

As used herein "Janus particle" refers to a particle whose surface has two or more distinct physical properties. A Janus particle may comprise a biomimetic particle, wherein the Janus particle comprises two distinct, bound ligand populations, thus possessing the properties and functionalities of the two bound ligand populations. The two ligand populations are generally arranged in a "bull's eye" configuration on a Janus particle, giving the particle biomimetic properties substantially similar to those of a natural antigen presenting cell. The term "bull's eye" configuration refers to a patterning of ligand populations where one or more substantially concentric patterns of the first ligand population being surrounded by the second ligand population. In certain aspects, the second ligand populations does not significantly overlap with the concentric pattern formed by the first ligand population.

The term "modulating T cell activation," as used herein, refers to manipulating T cell signaling pathways, thereby affecting T cell activation. Preferably, the term refers to initiating signaling in T cells through the T cell activation pathway, involving simultaneous engagement of a T cell receptor and a costimulatory receptor. Examples of T cell costimulatory receptors include, but are not limited to, CD28, CTLA4, Inducible Costimulator (ICOS), and integrins, including but not limited to, VLA-4, VLA-5, and LFA-1. Modulation of T cell activation occurs at the T cell's T cell receptor (TCR) complex. A T cell TCR complex generally comprises the TCR, and CD3, and may comprise one or more costimulatory receptors.

"Particles," as used herein, generally refers to synthetic nano- or micro-sized particles of about 0.1 µm to about 100 µm in diameter. Particles used herein may be any size of about 0.1 µm and about 100 µm in diameter. In certain embodiments, particles are about 0.1 µm to about 20 µm in diameter. In other embodiments, particles are about 0.5 µm to about 5 µm in diameter. In a particular embodiment, particles are about 3 µm in diameter. The term "particles" may refer to a synthetic particle comprised of various materials, including but not limited to, silica, polystyrene, melamine resin, and polymethacrylate.

As used herein, the term "monolayer" when used to describe an arrangement of particles, refers to a single, closely packed layer of the particles.

As used herein, the term "substantially concentric" means a shape being approximately circular. A substantially concentric shape need not be perfectly circular, but may vary in radius as measured from points around the circumference of the shape. The term "substantially concentric" includes, but is not limited to, ellipses and ovoids. Further, a "substantially concentric" shape need not have a smooth circumference.

As used herein, "ultrapure water" refers to water that has been treated to the highest levels of purity for all types of contaminants including, but not limited to organic and inorganic compounds, dissolved and particulate matter, and dissolved gases.

"Solvent evaporation" refers to the process of applying a solvent containing a substance, such as microparticles, to a substrate and evaporating the solvent. Solvent evaporation can be employed to form a monolayer of microparticles on a substrate.

"Dip coating" refers to the process of introducing a substrate to a colloidal suspension comprising particles, such as microparticles, and withdrawing the substrate, thereby forming a uniform liquid film containing microparticles. Following evaporation of a solvent, a uniform monolayer of microparticles remains on the substrate.

As used herein, the term "about" refers to an amount varying from the stated value or range by $1/10$ of the stated value or range, but is not intended to limit any value or range of values to only this broader definition. For example, a microparticle having a diameter of about 3 µm includes microparticles having diameters of 2.7 to 3.3 µm. Each value or range of values preceded by the term "about" is also intended to encompass the embodiment of the stated absolute value or range of values.

As used herein, the term "immunotherapy" refers to a therapy that induces, enhances, or suppresses the immune response in a subject. In particular embodiments, an immunotherapy may include, but is not limited to, adoptive immunotherapy, tolerance induction in an immune disease, autologous immune enhancement, and viral infection immunotherapy. In particular embodiments, an immunotherapy is administered to a subject enterally, parentally, intramuscularly, intravesically, subcutaneously, or transmucosally.

As used herein, "adoptive immunotherapy" refers to an immunotherapy wherein immune-derived cells are transferred into a subject with the goal of transferring the immunologic functionality and characteristics of the transferred immune-derived cells into the subject. Adoptive immunotherapy may be harnessed to treat a number of conditions, including but are not limited to, cancer, autoimmune disease, and viral infection, as well as to induce tolerance in autoimmune disease.

As used herein, "tolerance induction" refers to the initiation or causing of refractivity to activating receptor-mediated stimulation. Such refractivity is generally antigen-specific and persists after exposure to a tolerizing antigen has ceased. Tolerance to self-antigens or to foreign antigens can be induced. In one particular embodiment, a tolerant subject does not produce an adverse immune response to a self-antigen over a period of time after treatment with a T cell activated by a biomimetic particle described herein ceases, even when challenged with the antigen, and remains capable of providing an immune response against other antigens.

As used herein, "autologous immune enhancement therapy" refers to a particular adoptive immunotherapy wherein immune-derived cells are taken from a subject (autologous cells), cultured, and processed to activate the cells, and then reintroduced into the subject. In particular embodiments, the autologous cells are activated by a biomimetic particle described herein.

As used herein, "viral infection immunotherapy" refers to the use of immune derived cells as a therapeutic to initiate or supplement an immune response in a subject suffering from a viral infection. In particular embodiments, the immune-derived cells used in a viral infection immunotherapy are heterologous antigen-specific cells. Preferably, the immune-derived cells used in a viral infection immunotherapy are autologous antigen-specific cells. Immune derived cells used in a viral infection immunotherapy are preferably activated by a biomimetic particle described herein.

"Preparative lymphodepletion" refers to the temporary ablation of the immune system of a subject in preparation for an immunotherapy (e.g., adoptive cancer immunotherapy). Total-body irradiation or chemotherapy can be used to deplete lymphoid cells. Preparative lymphodepletion is known to augment the efficacy of tumor-specific T cells in the lymphopenic environment. Preparative lymphodepletion has been further shown to enhance the effectiveness of adoptive immunotherapy by depleting endogenous cells that compete for activating cytokines, and by depleting endogenous regulatory T cells which diminish the effectiveness of the therapy.

"Autologous T cells" are T cells derived from the same subject to which the T cells will be reintroduced.

"Heterologous T cells" are T cells derived from a source other that the subject to which the T cell will be introduced.

General Description

T cells are activated when T cell receptors (TCRs) and the co-receptors bind their respective ligands on the surface of antigen presenting cells (APCs). The initial ligand-receptor recognition leads to the formation of a micron-sized membrane junction known as the immunological synapse. As T cell signaling proceeds, ligand-bound membrane receptors and signaling proteins, such as TCRs, co-stimulatory receptors and adhesion molecules, are clustered and reorganized in the synapse to form a pattern of several distinct concentric domains (FIG. 1A). Ligand-bound TCRs are transported from the cell periphery to accumulate in the central domain of the immunological synapse, while integrins and many cytoskeletal proteins are enriched in a ring structure surrounding the TCRs. The protein spatial organization is a reflection of long-range molecular interactions that take place in T cell activation. Additionally, the immunological synapse formation, by controlling which proteins come together and when they are apart, is a regulatory checkpoint for T cell stimulation.

Synthetic particles that display well-defined antigens and co-stimulatory ligands have been developed as artificial APCs (aAPCs) to stimulate T cell activation in vitro. These aAPCs have been designed to mimic different aspects of the native APCs, including size shape, ligand mobility, and multivalency. However, current design of these aAPCs has mainly focused on particles that have uniformly distributed ligands. Yet, T cell activation is known to involve spatial segregation of proteins. And while two-dimensional studies have demonstrated a potential for modulating T cell activation by spatially manipulating the immunological synapse formation, they cannot mimic the three-dimensional structure of native APCs.

The data disclosed herein demonstrates the ability of ligands patterned on nano- or micro-sized particles to mimic either the native or reverse immunological synapse (FIG. 1B), resulting in effective artificial APCs (aAPCs). The biomimetic aAPCs described herein, or biomimetic Janus particles, are useful in the activation of T cells in vitro. The activated T cells are useful in various T cell-based immunotherapies.

Named after the two-faced Roman god, Janus particles, by possessing distinct surface makeups or compartments in one entity, offer many promising biomedical applications that are not possible with homogeneous particles. For example, multicompartmental Janus particles have been developed as drug delivery carriers that allow controlled step-wise drug release. Multiplexed biomolecular detection is possible when one side of a Janus particle captures analytes while the other side is graphically encoded. Janus particles that are half-magnetic and half-fluorescent enable simultaneous imaging and magnetic therapy. Bi-functionality of Janus particles can also be exploited for simultaneous imaging/sensing. A new application of Janus particles as aAPCs for immune cell activation is described herein.

Figure 1B:
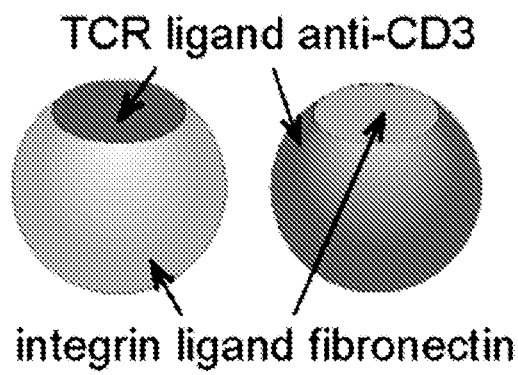

Bull's eye protein patterns that mimic either the native or reverse immunological synapse on the surface of micron-sized Janus particles are described herein (FIG. 1B). The two types of patterned particles activate T cells by directing the spatial organization of signaling proteins. The native and reverse bull's eye protein patterns described herein are shown herein to direct intracellular clustering of signaling proteins, such as actin and protein kinase C (PKC)-θ. T cell signaling, as indicated by intracellular calcium ion elevations, also differed depending on the ligand pattern. The data presented herein demonstrates the ability to use micropatterned Janus particles as aAPCs to modulate T cell signaling and activation.

In certain embodiments, a biomimetic Janus particle comprises a substantially concentric deposition of a first ligand population surrounded by a second ligand population. In other embodiments, the biomimetic Janus particle comprises two or more substantially concentric depositions of the first ligand population. When two or more substantially concentric depositions are of the first ligand population are present, they are interspersed, or "filled in," by the second ligand population.

The size of the substantially concentric deposition of the first ligand population is to be selected to approximate the size of an immunological synapse. In a human subject, the diameter of an immunological synapse of a T cell is about 1-3 μm. While the deposition of the first ligand population does not have to be circular, its approximate diameter can range between about 10 nm to about 5 μm. In certain embodiments, the approximate diameter of the deposition of the first ligand population is about 0.5 μm to about 3.5 μm. In a particular embodiment, the approximate diameter of the deposition of the first ligand population is about 1.7 μm.

First and second ligand populations are generally comprised of one or more ligands involved in T cell activation, one or more molecules to which a ligand involved in T cell activation may be bound, or a combination thereof. Ligands involved in T cell activation include, but are not limited to anti-CD3 antibodies, anti-CD28 antibodies, anti-TCR antibodies, anti-CTLA4 antibody, and ligands comprising a general integrin-binding motif. Anti-CD3 antibodies include any antibody or other ligand capable of binding to a CD3 subunit (γ, δ, or ε) or CD3 subunit dimer (ε/γ or ε/δ). Anti-CD28 antibodies include any antibody or other ligand capable of binding to CD28. Anti-TCR antibodies include any antibody or other ligand capable of binding at least one T cell receptor subunit (α and β). Anti-CTLA4 antibodies include any antibody or other ligand capable of binding to CTLA4 (CD152). Anti-CTLA4 antibodies further include any antibody or other ligand capable of blocking CTLA4 (CD152) signaling. Ligands comprising a general integrin-binding motif include, but are not limited to fibronectin, collagen, laminin, vitronectin, fibrinogen, and thrombospondin. Molecules to which a ligand involved in T cell activation, include, for example, biotin. An antibody or other ligand described herein can be conjugated with streptavidin and incubated with a biomimetic Janus particle comprising biotin. The streptavidin-conjugated antibody or other ligand with then be bound to biotin via biotin's strong interaction with streptavidin. Alternatively, a biomimetic Janus particle comprising biotin can be incubated with streptavidin, followed by incubation with a biotinylated antibody or other ligand.

The first and second ligand populations can comprise of one or more ligands. Generally, the first and second ligand populations will differ in their composition by at least one ligand. In certain embodiments, the first and second ligand populations will not share any common ligands. In yet other embodiments, the first and second ligand populations comprise of a single type of ligand. In certain aspects, only one of either the first ligand population or second ligand population will comprise an integrin-binding ligand. In a particular aspect, one of either the first ligand population or second ligand population comprises the integrin-binding ligand fibronectin.

As described above, the biomimetic Janus particle's first and second ligands are arranged either in a natural or reverse bull's eye configuration, simulating either the natural or reverse organization of ligands in an immunological synapse of a natural antigen presenting cell. In an embodiment employing the natural bull's eye configuration, the first ligand population comprises at least one ligand capable of binding to at least one component of a T cell TCR complex, such as, for example, an anti-CD3 antibody, an anti-CD28 antibody, an anti-TCR antibody, or an anti-CTLA4 antibody. In the natural bull's eye configuration, the first ligand population can alternatively comprise one or more molecules to which a ligand capable of binding to at least one component of a T cell TCR complex may be bound. For example, the first ligand population can comprise biotin. A streptavidin-conjugated ligand capable of binding to at least one component of a T cell TCR complex can then be bound to biotin. In the natural bull's eye configuration, the second ligand population comprises at least one ligand comprising a general integrin-binding motif. In a particular embodiment, the first ligand population comprises an anti-CD3 antibody and the second ligand population comprises fibronectin. In another particular embodiment, the first ligand population comprises biotin, and the second ligand population comprises fibronectin. An anti-CD3 antibody can bound to biotin through a biotin-streptavidin interaction.

In an embodiment employing the reverse bull's eye configuration, the first ligand population comprises at least one ligand comprising a general integrin-binding motif, while the second ligand population comprises at least one ligand capable of binding to at least one component of a T cell TCR complex. In the reverse bull's eye configuration, the second ligand population can alternatively comprise one or more molecules to which a ligand capable of binding to at least one component of a T cell TCR complex may be bound. For example, the second ligand population can comprise biotin. A streptavidin-conjugated ligand capable of binding to at least one component of a T cell TCR complex can then be bound to biotin. In a particular embodiment, the first ligand population comprises fibronectin, and the second ligand population comprises an anti-CD3 antibody. In another particular embodiment, the first ligand population comprises fibronectin, and the second ligand population comprises biotin. An anti-CD3 antibody can bound to biotin through a biotin-streptavidin interaction.

The two types of patterned particles differentially direct the signaling proteins of T cells. When exposed to the reverse bull's eye configuration, T cells exhibited annular or diffusive accumulation of actin whereas the native bull's eye configuration exhibited either focal or diffusive accumulation of actin. Control T cells stimulated with particles having uniform presentation of anti-CD3 and fibronectin displayed only diffusive accumulation of PKC-θ. Similar results were observed with actin.

The data show that patterned particles modulate T cell activation from the outside in, so that the reverse bull's eye pattern, by preventing T cell receptors and other signaling proteins from moving to the center of the immunological synapse, activates T cells more robustly than the native pattern. Therefore, in a particular embodiment, T cells are activated by biomimetic Janus particles patterned with a reverse bull's eye pattern. In another particular embodiment, biomimetic Janus particles patterned with the native bull's eye pattern are used to suppress an immune response.

The first and second ligand populations are patterned on nano- or micro-sized particles. The nano- or micro-sized particles can be any particle capable of binding one or more ligands. Nano- or micro-sized particles useful as a base for biomimetic Janus particles described herein include, but are not limited to, silica particles, polystyrene particles, melamine resin particles, and polymethacrylate particles. In certain embodiments, the nano- or micro-sized particles are silica particles.

Particles use as a base for biomimetic Janus particles described herein generally have a diameter of about 0.1 μm to about 20 μm. Particles can be larger or smaller than this, but any such particle will not resemble the size of a natural APC. In certain embodiments, particles have diameters of about 0.5 μm to about 5 μm. In one particular aspect, particles have a diameter of about 3 μm.

The biomimetic Janus particles described herein may be synthesized by many different methods. These methods include, but are not limited to, microcontact printing, nanolithography, microlithography, and co-polymer self-assembly. Biomimetic Janus particles having either a native or reverse bull's eye ligand pattern may be synthesized by any one of these methods, or a combination thereof. The method of nano- or microlithography can be any such method known in the art, such as photolithography, electron beam lithography, nanoimprint lithography, interference lithography, X-ray lithography, extreme ultraviolet lithography, magnetolithography, and dip-pen lithography. Methods of self-directed co-polymer assembly utilizing block co-polymers can also be used to synthesize biomimetic Janus particles. Any of these methods can be used, where the method is capable of patterning one or more substantially concentric depositions of a first ligand population on a nano- or micro-sized particle. In certain embodiments, each substantially concentric deposition of the first ligand population has a diameter of about 10 nm to about 5 μm. In certain embodiments, the approximate diameter of the deposition of the first ligand population is about 0.5 µm to about 3.5 µm. In a particular embodiment, the approximate diameter of the deposition of the first ligand population is about 1.7 µm. In particular aspects, biomimetic Janus particles having either a native or reverse bull's eye pattern are synthesized by microcontact printing.

Generally, a biomimetic Janus particle is synthesized by forming at least one substantially concentric pattern of a first ligand population on an appropriate nano- or microparticle. After forming the substantially concentric pattern(s) of the first ligand population on the particle, the particle is then incubated with a second ligand population, so as to surround the substantially concentric pattern(s). It is preferable, although not required, that the second ligand population not substantially overlap the substantially concentric pattern(s) of the first ligand population.

Characteristics of particles and ligand populations useful in the synthesis of biomimetic are, unless otherwise noted, the same as those described above for a biomimetic Janus particle. For example, silica, polystyrene, melamine resin, or polymethacrylate particles having a diameter of about 0.1 µm to about 20 µm can be used in the methods described herein. First and second ligand populations useful for the synthesis of a biomimetic Janus particle are the same as those described above.

Optionally, two or more substantially concentric patterns of the first ligand population are formed on a particle. The two or more substantially concentric patterns of the first ligand population are surrounded by the second ligand population. In certain embodiments, each substantially concentric deposition of ligand population comprises a single type of ligand. Having multiple substantially concentric patterns of the first ligand population deposited on the particle has the benefit of increasing the probability of a T cell interacting with the native or reverse immunological synapse-mimicking bull's eye pattern formed on the particle.

Where biomimetic Janus particles are patterned via microcontact printing, a monolayer of particles is first deposited on a substrate, such as glass. As discussed and described above, particles of various sizes and materials can be used. Where a monolayer of particles is to be formed on a substrate, as in microcontact printing, it is beneficial to supply particles of substantially the same diameter. This can help to ensure the deposition of a uniform monolayer on the substrate and to help ensure consistent microcontact printing. Particles can be cleaned prior to the formation of the monolayer on a substrate. Many different solvents can be used to clean particles, including water. Preferably, the solvent used to clean particles removes organic residues from the particles. In some embodiments, the solvent is a strong oxidizing agent capable of both removing organic residues and hydroxylating the surface of the particles, making them hydrophilic. In one embodiment, the solvent used to clean the particles is piranha solution comprising $H_2SO_4/H_2O_2$.

The substrate can be cleaned prior to the formation of the monolayer of particles thereon. Similarly to the particles, many different solvents can be used to clean the substrate. Preferably, a solvent used to clean the substrate removes organic residues. In some embodiments, the solvent is a strong oxidizing agent capable of both removing organic residues and hydroxylating the surface of the substrate, making it hydrophilic. In one embodiment, the solvent used to clean the substrate is piranha solution comprising $H_2SO_4/H_2O_2$. Optionally, the substrate is cleaned while being maintained at an elevated temperature of about 30 to 100° C. In one aspect, the substrate is cleaned with piranha solution at a temperature of about 75° C. The substrate is cleaned for a period of time sufficient to remove organic residues and hydroxylate the surface of the substrate. The period of time sufficient for cleaning will depend on the solvent used, and can be adjusted to ensure adequate cleaning. For example, where the cleaning solvent is piranha solution, the substrate is cleaned for at least 5 minutes. In one aspect where the substrate is cleaned with piranha solution, the substrate is cleaned for about 15 minutes.

Following any substrate cleaning step, the substrate is rinsed in order to remove the solvent from the substrate. The cleaned substrate can be cleaned, for example, using distilled or ultrapure water.

Monolayers of particles may be formed on a substrate by any means known in the art, including but not limited to, solvent evaporation and dip coating.

A form of soft lithography, microcontact printing utilizes a polymer stamp coated, or "inked," with substance, to form patterns on the surface of a substrate. In its use to synthesize biomimetic Janus particles, a polymer stamp inked with a first ligand population is contacted with the monolayer of particles, which acts as the microcontact printing "substrate." Due to particles being spherical, this contacting step results in a substantially concentric deposition of the first ligand population being made on each particle of the monolayer contacted with the inked polymer stamp. Polymers useful for the microcontact printing of biomimetic Janus particles include, but are not limited to, silicon-based organic polymers and hydro-gel-forming polymers. These polymers may be toughened or hardened ("cured") by cross-linking polymer chains. In particular aspects, polydimethylsiloxane (PDMS) is used as the polymer stamp.

A cured polymer stamp is generally cut from a larger piece of cured polymer, although cured polymer stamps of a particular size can be formed directly. In some embodiments, the cured polymer stamp has a surface area of about 0.5 to about 10 $cm^2$. In one aspect, the section of cured polymer has a surface area of about 1 $cm^2$. In one particular embodiment, the section of cured polymer comprises PDMS having a surface area of about 1 $cm^2$.

A section of cured polymer can be treated in order to make the surface of the section of cured polymer hydrophilic, which facilitates the coating or "inking" step, allowing the first ligand population to more easily adsorb to the surface of the cured polymer stamp. Treatment of the cured section can included treatment with a strong oxidizing agent capable of hydroxylating the surface of the section of cured polymer, thereby making the treated surface of the section of cured polymer hydrophilic. In a particular embodiment, a cured section of polymer is hydroxylated by treating it with piranha solution comprising $H_2SO_4/H_2O_2$. The strength of the oxidizing agent can be adjusted to achieve a desired result. For example, in one embodiment, the piranha solution comprises a 3:1 solution of $H_2SO_4/H_2O_2$.

Before pressing the section of cured polymer onto the monolayer of particles, the section of cured polymer is first "inked," or coated, with a ligand. Contacting the section of inked, cured polymer with the particles thereafter causes the individual particles of the monolayer of particles to partially embed in the inked, cured polymer. Removing the particle from the inked, cured polymer leaves a substantially concentric deposit of ligand on the particle.

The section of cured polymer is inked with a first ligand population as described above. Briefly, the first ligand population comprises one or more ligands such as an anti-CD3 antibody, an anti-CD28 antibody, an anti-TCR antibody, an anti-CTLA4 antibody, a ligand comprising a general integrin-binding motif, or biotin. The section can also be inked with any other ligand not listed that is known to be involved in T cell activation at the immunological synapse. The section of cured polymer may be inked with the ligand by incubating the section of cured polymer, or a surface thereof, in the ligand. Where the particles are to be patterned with a natural bull's eye pattern, the first ligand population comprises a ligand capable of binding to at least one component of a T cell TCR complex, such as an anti-CD3 antibody, or biotin. As described above, through a biotin-streptavidin interaction, a ligand capable of binding to at least one component of a T cell TCR complex can then be bound to biotin. In other embodiments, where the particles are to be patterned with a reverse bull's eye pattern, the section of cured polymer is inked with a first ligand population comprising at least one ligand having a general integrin-binding motif.

Prior to contacting the inked section of cured polymer with the monolayer of particles, the inked section of cured polymer may be dried. Drying the inked, cured section of polymer results in a more precise and controllable transfer of the ligand from the inked section of cured polymer to the particles. An inked, cured section of polymer can be dried, for example, under a stream of nitrogen prior to pressing the section onto a monolayer of particles.

To transfer the ligand population bound (inked) to the section of cured polymer, the inked section of cured polymer is contacted with the monolayer of particles. This is done under a known pressure, which allows for the control of the diameter of the substantially concentric area of ligand deposited on a particle. An increase in pressure will result in particles being further embedded in the section of cured polymer, resulting in deposition of a substantially concentric pattern having a larger diameter. The diameter of the substantially concentric area of ligand deposited on a particle can also be controlled by controlling the stiffness of the cured polymer, where under the same applied pressure, a softer polymer will result in a substantially concentric pattern having a larger diameter. Methods of controlling the stiffness of a cured polymer are known in the art. For example, the ratio of monomer to crosslinker can be adjusted to provide a polymer of desired stiffness.

In certain embodiments, the cured section of polymer incubated with the first ligand is pressed against the monolayer of particles at a pressure of about $0.5 \times 10^4$ to $2.5 \times 10^4$ Pa. In a particular embodiment, pressing a section of inked, cured PDMS prepared as described in the Examples, against a monolayer of particles at a pressure of $1.5 \times 10^4$ results in the deposition of a substantially concentric pattern of about 1.7 μm on the particle, which is a similar size to the central protein domain found in the immunological synapse. Utilizing a lesser pressure will generally result in a substantially concentric area of ligand having a smaller diameter, as will using a stiffer section of polymer. Utilizing a higher pressure, or a softer polymer, will generally result in a substantially concentric area of ligand deposited on the particle to have a larger diameter.

The pressure applied to the inked, cured section of polymer, the stiffness of the section of polymer, or a combination thereof, can be adjusted to provide a substantially concentric deposition of the first ligand population on a particle having a diameter of about 10 nm to about 5 μm. In certain aspects, the substantially concentric deposition of the first ligand population on the particle is about 0.5 to about 3.5 μm. In a particular embodiment, the substantially concentric deposition of the ligand on a particle mimics the diameter of an immunological synapse of a T cell of a subject. In a human subject, the diameter of an immunological synapse of a T cell is about 1-3 μm. Therefore, in a particular embodiment, a section of cured PDMS inked with a ligand is used to generate a substantially concentric deposition of ligand on a particle, wherein the substantially concentric deposition of ligand on the particle has a diameter of about 1 to about 3 μm.

Following contacting the inked, cured section of polymer with the monolayer of particles, the monolayer of particles is removed from the substrate, and the particles are incubated in a second ligand. The particles can either remain embedded in the inked, cured section of polymer during incubation with the second ligand population, or can be released from the inked cured section of polymer prior to incubation with the second ligand population. In either instance, the second ligand will adsorb to the particle, surrounding the substantially concentric pattern of first ligand deposited on the particles by the inked, cured section of polymer. Where particles remain embedded in the inked, cured section of polymer, following incubation with the second ligand population, the particles are released from the inked, cured section of polymer. Embedded particles can be released by, for example, sonication. Optionally, where particles remain embedded in the inked, cured section of polymer during incubation with the second ligand population, the released particles are re-incubated with the second ligand population. This second incubation with the second ligand population minimizes any gaps between the first ligand population and the second ligand population that can occur when the particles are incubated with the second ligand population while still embedded in the inked, cured section of polymer.

Where the particles are to be patterned with a natural bull's eye pattern, the second ligand population comprises at least one ligand having a general integrin-binding motif. In other embodiments, where the particles are to be patterned with a reverse bull's eye pattern, the second ligand population comprises at least one ligand capable of binding to at least one component of a T cell TCR complex, such as an anti-CD3 antibody, or biotin. As described above, through a biotin-streptavidin interaction, a ligand capable of binding to at least one component of a T cell TCR complex can then be bound to biotin.

Incubation with the second ligand population is for a period of time to allow for the second ligand population to adsorb to particle. In certain embodiments, incubation with the second ligand population is for about 0.5 to about 3 hours. In a particular embodiment, incubation with the second ligand population is for about 1.5 hours.

Optionally, after particles have been patterned with the first and second ligands, and, if embedded in the inked, cured section of polymer, have been released from the same, the patterned particles can undergo passivation, for example, by treating the particles with PBS buffer comprising bovine serum albumin.

Figure 1C:
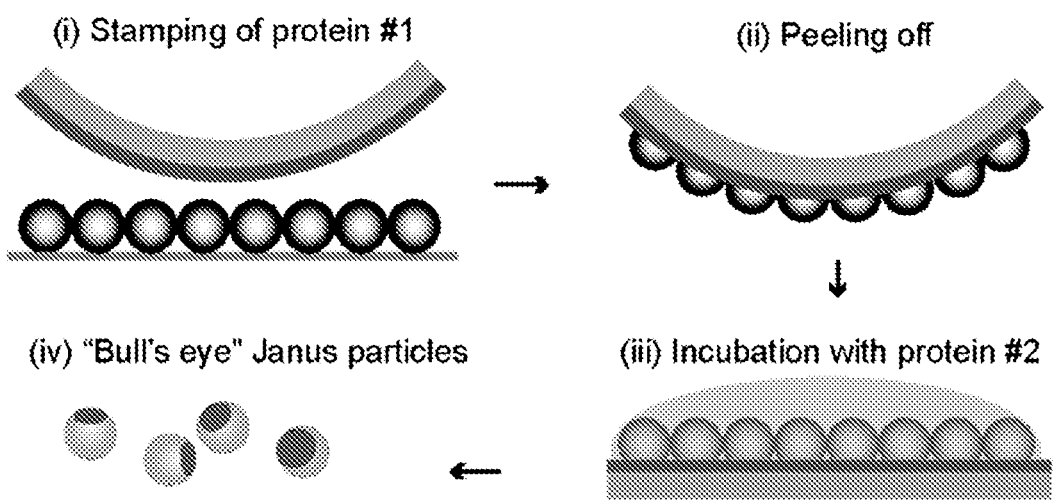
FIG. 1C: "Bull's eye" Janus particles resemble protein patterns in the immunological synapse. Schematic representation of the microcontact printing of "bull's eye" patterns on particles.
Figure 1D:
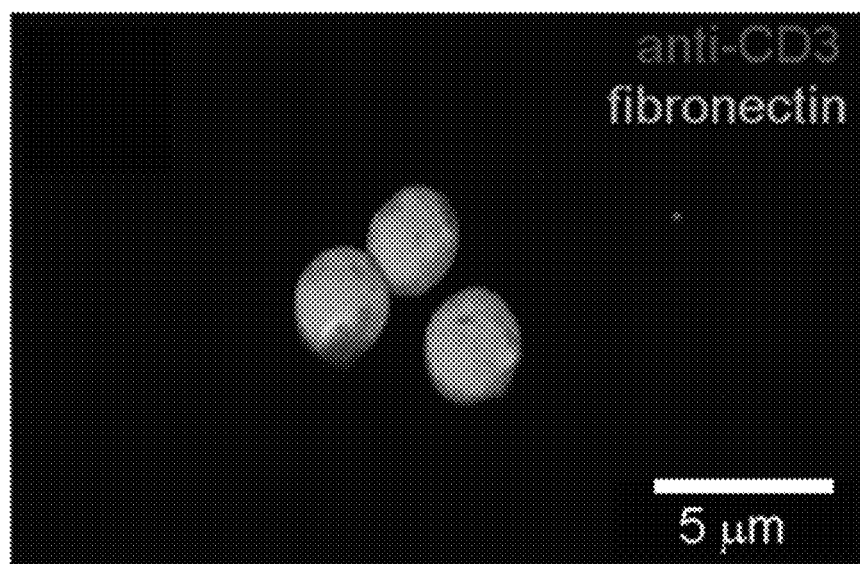
FIGS. 1D-1E: "Bull's eye" Janus particles resemble protein patterns in the immunological synapse. 3-D confocal fluorescence images of the "bull's eye" Janus particles.
Figure 1E:
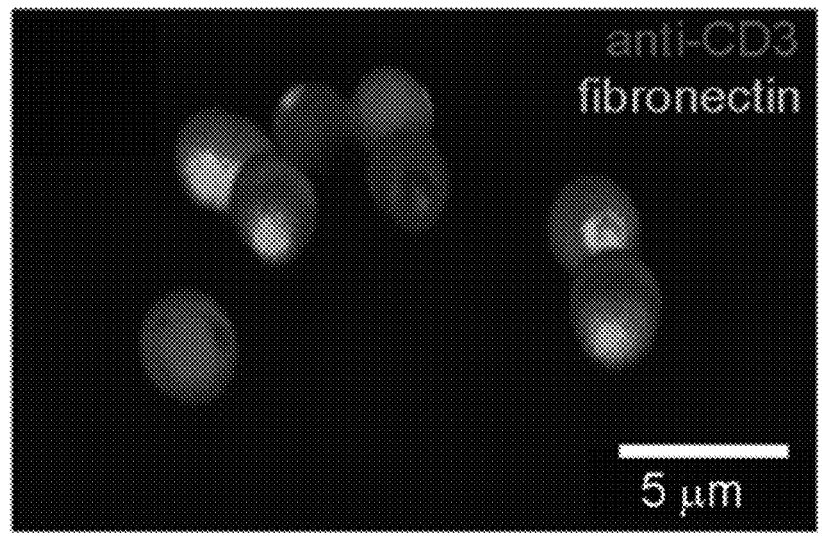
Figure 1F:
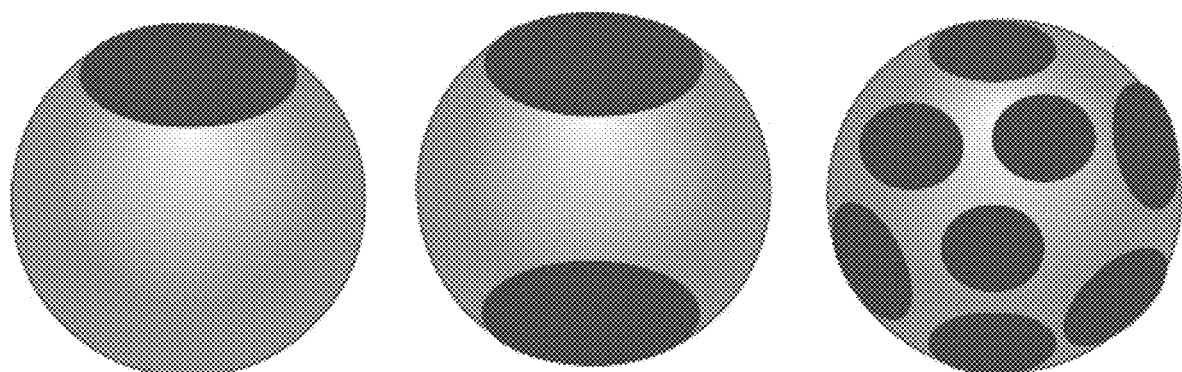
FIG. 1F: Schematic representation of "bull's eye" Janus particles possessing either one, two, or multiple substantially concentric patterns of a first ligand (red) surrounded by a second ligand (green).

Optionally, the process of contacting an inked, cured section of polymer with a particle is repeated one or more times, releasing the particle from the inked, cured section of polymer between each repetition. Following contacting a particle two or more times with an inked, cured section of polymer, the particle is incubated with the second ligand population. This process results in two or more substantially concentric depositions of first ligand population surrounded by a second ligand population (FIG. 1F). In another embodiment, a different first ligand is inked on a cured polymer for use in the repeated contacting step, wherein each substantially concentric deposition of ligand population comprises a single type of ligand. Having multiple substantially concentric patterns of the first ligand population deposited on the particle has the benefit of increasing the probability of a T cell interacting with the native or reverse immunological synapse-mimicking bull's eye pattern formed on the particle.

In embodiments where either the first or second ligand population comprises biotin, particles to which biotin are bound are further incubated with either a streptavidin-conjugated ligand or simply with streptavidin. When simply incubated with streptavidin, a further incubation step with a biotinylated ligand is required. These steps result in binding one or more ligands involved in T cell activation to the particle via biotin.

In yet other embodiments, co-polymer self-assembly is employed to pattern at least one substantially concentric pattern of a first ligand population on a particle. In one embodiment, a first ligand population, as described above, is bound to a first block copolymer. The first block copolymer is combined with a second block copolymer to form a spherical biomimetic Janus particle having at least one substantially concentric pattern of the first ligand population.

The resulting spherical biomimetic Janus particle having at least one substantially concentric pattern of the first ligand population can then be incubated with a second ligand population, as described above. Alternatively, a second ligand population, can be bound to a second block copolymer prior to being combined with the first block copolymer. Combining the first block copolymer, to which is bound a first ligand population, with the second block copolymer, to which is bound a second ligand population, results in a spherical biomimetic Janus particles have at least one substantially concentric pattern of the first ligand population surrounded by the second ligand population.

In certain embodiments, the first and second block copolymers undergo directed self-assembly.

Also contemplated herein are biomimetic Janus particles produced by any of the methods described herein. Other aspects contemplated herein include a compound comprising one or more biomimetic Janus particles described herein and/or one or more biomimetic Janus particles produced by any of the methods described herein. Compounds comprising biomimetic Janus particles can be formulated for various applications such as, for example, in vitro activation of T cells.

Biomimetic Janus particles described herein, whether synthesized by a method described herein or not, are useful for activating a population of T cells in vitro. Efforts to amplify T cell response to diseases including cancer, autoimmune disease, and viral infection often focus on immunotherapies involving transferring activated T cells into a subject. Signals that T cells receive from native natural antigen presenting cell (APC) during and after their initial encounter with an antigen can influence their programming and subsequent therapeutic efficiency. The inability to regulate the signals and interactions provided by naturally occurring APCs has resulted in increased interest in the use of artificial APCs to allow for greater control over T cell signaling and facilitate the generation of optimally effective T cells for immunotherapy. In addition, isolation of native APCs for T cell-based immunotherapies is time-consuming, expensive, and difficult to reproduce.

It is known that T cell activation involves the spatial organization of ligands. Initial ligand-receptor recognition leads to the formation of a micron-sized membrane junction known as the immunological synapse. As T cell signaling proceeds, ligand-bound membrane receptors and signaling proteins, such as TCRs, co-stimulatory receptors and adhesion molecules, are clustered and reorganized in the synapse to form a "bull's eye" pattern of several distinct concentric domains (FIG. 1A). Ligand-bound TCRs are transported from cell periphery to accumulate in the central domain of the immunological synapse, while integrins and many cytoskeletal proteins are enriched in a ring structure surrounding the TCRs. The protein spatial organization is a reflection of long-range molecular interactions that take place in T cell activation. Additionally, the immunological synapse formation, by controlling which proteins come together and when they are apart, is a regulatory checkpoint for T cell stimulation.

T cells and other immune cells exhibit different levels of activation when they encountered micropatterned "islands" of protein ligands designed to separate or co-localize different membrane receptor on flat surfaces. Cell signaling is prolonged on micropatterned lipid bilayers on which transport of receptor-ligand pairs was constrained by metal grids. Ligand density and spacing, controlled by using nanoparticle arrays, also affect T cell activation. Several studies involving two-dimensional surfaces have demonstrated the potential of modulating T cell activation by spatially manipulating the immunological synapse formation. However, these two-dimensional arrangements do not mimic the three-dimensional structure of native APCs The biomimetic Janus particles described herein either mimic the ligand organization found in a native immunological synapses, or are arranged in reverse relative to a native immunological synapse. The biomimetic Janus particles described herein are useful for activating T cells in vitro. T cells, once activated in vitro by a biomimetic Janus particles described herein, may be used in an immunotherapy in a subject in need thereof.

T cells can be activated by one or more biomimetic Janus particles described herein. In particular, the biomimetic Janus particles described herein are useful for activating T cells in vitro. T cells activated in vitro by biomimetic Janus particles described herein can be used in an immunotherapy administered to a subject in need thereof.

T cells derived from several sources can be cultured, activated by biomimetic Janus particles described herein, and utilized in an immunotherapy. T cells to be activated can be autologous T cells isolated from a subject in need of an immunotherapy, heterologous T cells derived from a source other than the subject in need of an immunotherapy, or a combination thereof. Naïve T cells, $CD8^+$ T Cells, $CD4^+$ T cells, or any combination thereof, can also be activated by biomimetic Janus particles described herein.

In certain embodiments, the T cells to be activated are antigen-specific T cells. Antigen-specific T cells can be generated by methods known in the art, including but not limited to, identifying and cloning T cells from subjects with particularly good antigen responses, generating chimeric antigen receptors and transfecting cultured T cells with the chimeric antigen receptor specific for a particular antigen of interest, and isolating T cell receptors from humanized mice that have been primed to recognize a particular antigen of interest, wherein the mice express human MHC class I or MHC class II molecules and can be immunized with the particular antigen of interest, and wherein mouse T cells specific for the MHC-restricted epitope of interest can then be isolated, and their TCR genes cloned into recombinant vectors that can be used to genetically engineer cultured T cells. In one preferred embodiment, the T cells are tumor-antigen specific T cells.

To activate T cells using biomimetic Janus particles described herein, the biomimetic Janus particles are added to cultured T cells. The cultured T cells are incubated with the biomimetic Janus particles for about 5 minutes to about 2 weeks to allow activation. The biomimetic Janus particles interact with the cultured T cell, mimicking the immunological synapse formation between a T cell and a natural antigen presenting cell. The biomimetic Janus particles direct T cell protein movement and signaling to activate the T cell. In certain embodiments, cultured T cells are incubated with the biomimetic Janus particles described herein for about 1 to about 60 hours, or for about 24 to about 48 hours.

The population of cultured T cells can be rinsed following incubation with the biomimetic Janus particles described herein to remove the particles from the population of T cells. Rinsing is preferable when the T cells are to be introduced into a subject as part of an immunotherapy.

T cells activated by the biomimetic Janus particles described herein can be used in immunotherapies including, but not limited to adoptive immunotherapy for cancer, tolerance induction in autoimmune disease, autologous immune enhancement therapy, and viral infection immunotherapy. Such immunotherapies are known in the art (see, e.g., Restifo et al., (2012) Nat Rev Immunol, March 22; 12(4):269-81; Maus et al., (2014) Annu Rev Immunol, 32:189-225; Singer et al., (2014) Front Immun, 5:46). The biomimetic Janus particles described herein can be used or adopted for use in such therapies. Optionally, prior to administering an immunotherapy comprising administering activated T cells described herein to a patient, the patient is subjected to a step of preparative lymphodepletion (Gattinoni et al., (2006) Nat Rev Immunol, May; 6(5):383-93). Modifications to the biomimetic Janus particles can be made to tailor their use to a specific situation. Such modifications are contemplated herein, and do not depart from the essential scope of the present disclosure.

EXAMPLES

The materials, methods, and embodiments described herein are further defined in the following Examples. Certain embodiments of the present invention are defined in the Examples herein. It should be understood that these Examples, while indicating certain embodiments of the invention, are given by way of illustration only. From the discussion herein and these Examples, one skilled in the art can ascertain the essential characteristics of the present invention and without departing from the spirit and scope thereof, can make various changes and modifications of the invention to adapt it to various usages and conditions, such as for the use in activating T cells for the various immunotherapies described above.

Example 1—Materials and Methods

Reagents and Cells.

SPHERO™ silica particles (5% w/v) were purchased from Spheroptech Inc. (Lake Forest, Ill.). Bovine serum albumin (BSA) and BSA-biotin were purchased from Thermo Scientific (Waltham, Mass.). Biotin N-hydroxysuccinimide ester (biotin-NHS) was purchased from Sigma-Aldrich (St. Louis, Mo.). Anti-human CD3 (anti-CD3) OKT antibody was purchased from eBioscience (San Diego, Calif.) and conjugated with biotin-NHS. Phalloidin Alexa 647 conjugate was purchased from Cell Signaling Technology (Danvers, Mass.). Fibronectin (human) was obtained from BD Biosciences (San Jose, Calif.) and further conjugated with Alexa Fluor® 488 carboxylic acid, succinimidyl ester. Protein kinase C (PKC)-θ antibody (C-19) was purchased from Santa Cruz Biotech (Dallas, Tex.). Fluo-4 AM and Alexa Fluor® 647 Chicken Anti-Goat IgG (H+L) were purchased from Invitrogen (Eugene, Oreg.). Polydimethylsiloxane (PDMS; Sylgard 184) was obtained from Dow Corning (Midland, Mich.) and used at 2:1 (w:w) base-to-curing-agent ratio.

Jurkat T cells (clone E6-1) were originally purchased from ATCC (Manassas, Va.). Jurkat T cells were cultured in RPMI 1640 complete growth media supplemented with 10% fetal bovine serum (FBS), 1 mM sodium pyruvate, 100 units/mL penicillin, and 100 µg/mL streptomycin. Ultrapure water (resistivity of 18.2 MΩ·cm) was used. Calcium-containing imaging buffer (121 mM NaCl, 6 mM NaHCO$_3$, 5.4 mM KCl, 5.5 mM D-glucose, 0.8 mM MgCl$_2$, 25 mM HEPES, 1.8 mM CaCl$_2$, pH 7.4) was used for live cell imaging experiments. Live cell imaging chambers and temperature controllers were purchased from Bioptechs (Butler, Pa.).

Microcontact Printing of Janus Particles.

Glass microscope slides were treated with piranha solution of $H_2SO_4/H_2O_2$ (30%), 3:1 at 75° C. for 15 minutes and rinsed in ultrapure water. Silica particles of 3-µm in diameter were cleaned with piranha solution and deposited via solvent evaporation on a clean glass microscope slide to form a monolayer. Sylgard 184 base and curing agent were mixed at 2:1 (w:w) ratio in a plastic cup, poured into a flat petridish, degassed in vacuum until no bubbles were visible, and cured at 65° C. for 12 hours. Small sections of the PDMS stamp (1 cm×1 cm) were cut out and treated with piranha solution to make the surface hydrophilic.

To generate the reverse "bull's eye" pattern in which a fibronectin patch is surrounded by anti-CD3 molecules, the top surface of a PDMS stamp was incubated with Alexa Fluor® 488-fibronectin solution (2 µg/mL) for at least 20 minutes, dried under a stream of nitrogen, and immediately pressed against the monolayer of silica particles at a pressure of $1.5 \times 10^4$ Pa. After 3 minutes, the stamp with embedded silica particles was peeled off from the substrate and incubated with Alexa Fluor® 568-BSA-biotin solution (16.5 µg/mL) for 1.5 hours. Particles were sonicated off the PDMS stamp and harvested in 1×PBS buffer containing BSA (0.005%, w/v) for passivation.

Janus particles with the native "bull's eye" pattern were prepared through the same procedure using PDMS stamps inked with BSA-biotin. Many particles exhibited a gap between the BSA-biotin patch and fibronectin-covered surface after incubation with fibronectin because fibronectin molecules were prevented from adsorbing onto the particle surface near the PDMS stamp due to the large size. The gap was filled by additional incubation in a diluted fibronectin solution (1 µg/mL in 1×PBS buffer) for 2 hours. The Janus particles were then further functionalized with streptavidin (100 nM) and biotinylated anti-CD3 (20 nM).

Calcium Imaging and Analysis.

Jurkat T cells were serum starved in serum-free cell media at 37° C. for 2 hours before imaging. To load cells with the intracellular $Ca^{2+}$ indicator Fluo-4 AM, 1 million cells were incubated with 5 µg/mL Fluo-4 in serum-free cell media at 37° C. for 30 minutes, washed, and then incubated in serum-rich cell media at 37° C. for another 30 minutes to allow complete de-esterification of intracellular AM esters.

The Fluo-4 loaded T cells were suspended in 1× imaging buffer and added into an imaging chamber at 37° C. after the addition of Janus particles.

Concentrations of Janus particles and cells were kept the same in all experiments. Time-lapse multi-channel epifluorescence microscopy images were immediately taken with a Nikon Eclipse Ti microscope system that is equipped with an iXon3 EMCCD Camera (Andor Technology) and a Nikon Plan APO 40X/0.95 N.A objective or a Nikon Plan Apo 100X/1.49 N.A TIRF objective. Images were acquired with 100 ms exposure time and 2 s interval time Imaging chambers were maintained at 37° C. with a heater.

A Matlab script was used to quantify the fluorescence intensity of individual cells as a function of time. The algorithm detected the outline of individual cells and calculated the average fluorescence intensity per pixel for each cell. Cells that were not in contact with any particles were removed in image processing. Due to uneven loading of dyes into cells, some cells appeared brighter than others. A basal intensity was obtained by averaging the fluorescence intensity of the first 25 imaging frames before the first calcium peaks. The average fluorescence intensity of each cell was then normalized by the basal intensity to enable comparison of the calcium signaling between cells and samples.

Immunofluorescence Staining and Confocal Fluorescence Imaging.

Jurkat T cells were serum starved at 37° C. for 2 hours before mixing with particles. 5 million cells were mixed with Janus particles in 1× imaging buffer solution for 4 minutes before fixation. Cells were fixed with 2% (w/v) paraformaldehyde (PFA) on ice for 15 minutes, permeabilized with 0.01% Triton X-100 for a few seconds, and blocked with 1% bovine serum albumin (BSA) for 1 hour. Actin was stained by incubation with 0.32 µg/mL phalloidin-Alexa Fluor® 647 for 30 minutes at room temperature. To label PKC-θ, permeabilized cells were incubated with 1 µg/mL PKC-θ antibody at room temperature for 2 hours, washed with 1×PBS solution for 3 times, blocked with 1% BSA for 30 minutes, and incubated with 1 µg/mL Alexa Fluor® 647 Chicken Anti-Goat IgG (H+L) at room temperature for 1 hour.

Confocal scanning fluorescence imaging was done on a Nikon A1R-A1 confocal microscope system equipped with a Nikon 100× oil-immersed objective and a Hamamatsu C11440 camera (Light Microscopy Imaging Center, Indiana University). Alternative scanning mode was used to avoid possible crosstalk between the Alexa 568 and Alexa 647 channels. Z-scan stacks were acquired with a 0.15 µm z-axis increment. Images were analyzed with ImageJ software.

Example II—Design and Fabrication of Biomimetic Janus Particles

T cell receptors (TCRs) and integrins are two membrane receptors that are known to play important roles in T cell activation and in immunological synapse formation. Anti-CD3 antibodies and fibronectin molecules were used in this study as ligands for TCRs and integrins, respectively. Anti-CD3 crosslinks CD3 subunits in the TCR complex and triggers T cell activation. Fibronectin is an adhesion molecule that binds α4β1 and α5β1 integrins on the Jurkat T cell membrane.

Two types of "bull's eye" protein patterns were generated on microparticles. One pattern resembles the native immunological synapse, in which anti-CD3 is enriched in the central domain and fibronectin accumulates in the surrounding region. The other protein pattern is the reverse type, in which a patch of fibronectin is surrounded by a field of anti-CD3.

A microcontact printing method (FIG. 1C) was developed to fabricate the "bull's eye" Janus particles, such that the protein patches were of similar size to the protein domains of a native immunological synapse. Firstly, a monolayer of 3-µm silica particles was deposited on a flat substrate. To generate the native "bull's eye" pattern, a BSA-biotin patch was generated by bringing a polydimethylsiloxane (PDMS) stamp that was "inked" with BSA-biotin solution into brief contact with the particles. The PDMS stamp was then lifted, removing the monolayer from the substrate, leaving partially embedded particles in the stamp. The exposed surfaces of the partially embedded particles were subsequently coated with fibronectin by incubation.

Janus particles with the reverse "bull's eye" pattern were fabricated using the same general procedure, during which the fibronectin patches were printed with a PDMS stamp, followed by BSA-biotin adsorption onto the exposed surface of particles. For both native and reverse bull's eye patterns, biotinylated anti-CD3 was conjugated with BSA-biotin via streptavidin linkers.

Figure 4A:
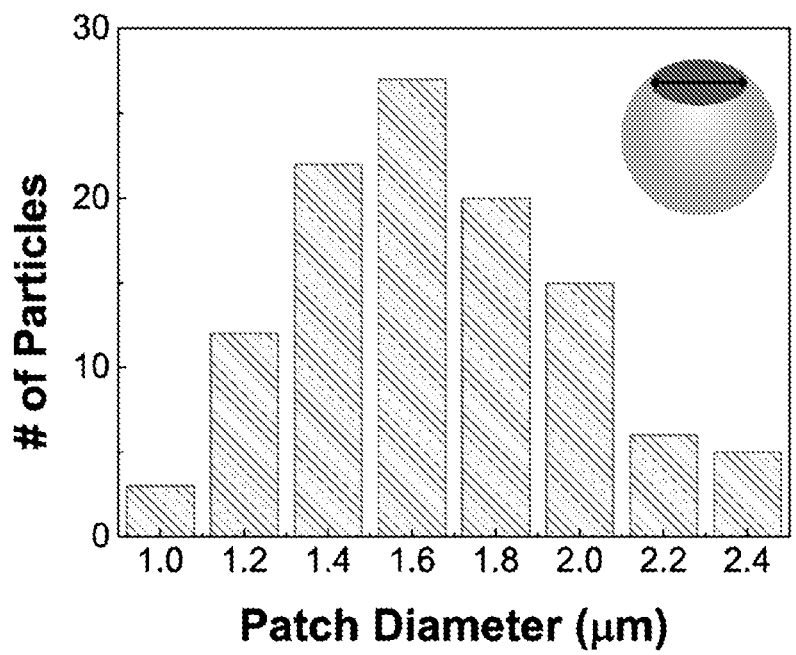
FIGS. 4A-4B: Bar graphs showing size distribution of anti-CD3 (FIG. 4A) and fibronectin (FIG. 4B) patches.
Figure 4B:
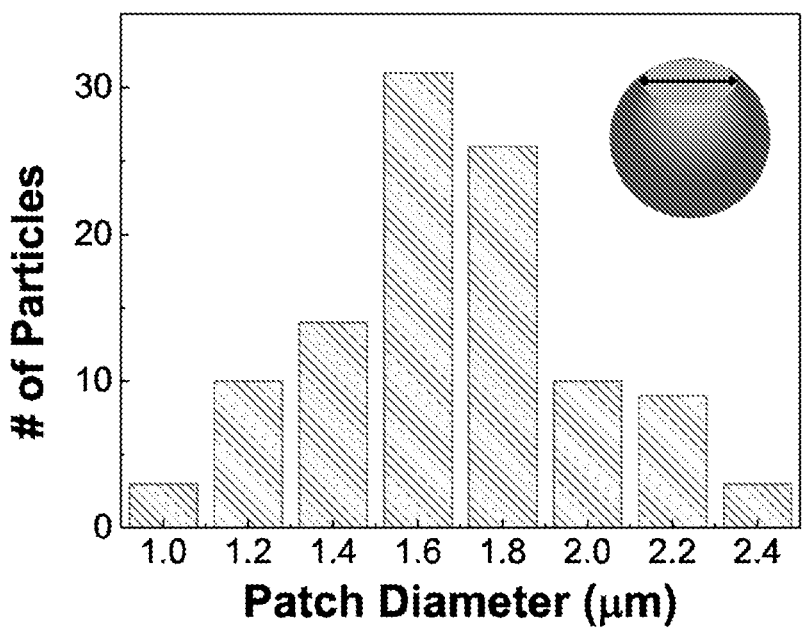

The size of protein patches can be adjusted by altering the stiffness of PDMS stamps, with softer stamps generating larger patches. In a particular experiment, a relatively hard stamp made of 2:1 monomer-to-crosslinker ratio resulted in protein patches having average diameters of (1.7±0.3) µm (FIG. 4), a similar size to the central protein domain found in the native immunological synapse. The morphology of the native and reverse "bull's eye" patterns was confirmed using 3-D fluorescence confocal scanning microscopy (FIGS. 1D-1E). Those images also show that cross-contamination of the two protein domains was negligible.

The spatial organization of proteins in T cells was determined to follows the patterns of anti-CD3 and fibronectin on the Janus particle surface. The clustering of two intracellular signaling proteins, actin and protein kinase C (PKC)-θ, was examined Neither of the proteins are membrane bound, but are known to be associated with TCRs and spatially segregate in the immunological synapse. Specifically, actin is a cytoskeletal network that supports clustering and translocation of membrane receptors including TCRs. Actin distributes across the entire immunological synapse at the beginning of T cell activation, but accumulates in a ring structure around the central accumulation of TCRs in the mature synapse. PKC-θ is a signaling protein required for T cell activation and survival; its intracellular clustering follows TCRs at initial T cell activation.

Example III—Activation of T Cells by Biomimetic Janus Particles

Figure 2A:
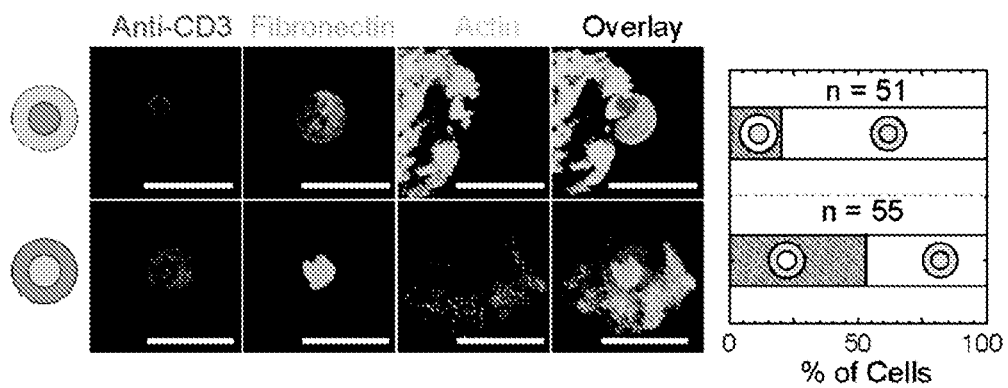
FIGS. 2A-2B: 3-D fluorescence confocal images show the intracellular clustering of actin (FIG. 2A) and protein kinase C (PKC)-θ (FIG. 2B) in T cells that were stimulated by the "bull's eye" Janus particles described herein. Clustering morphologies of actin and PKC-θ are summarized into three categories: focal, diffusive, and annular, as indicated by the schematic symbols in the bar graphs on the right of each figure. The blue color in each symbol indicates the localization of either actin or PKC-θ with respect to the "bull's eye" pattern on the particles. Scale bars: 5 µm.

In order to capture the early TCR activation stage and to prevent complete engulfment of particles, Jurkat T cells were fixed at 4 minutes after mixing them with particles. Cells that faced the "bull's eye" patterns were observed for data collection, although particles interacted with cells at random orientations. Morphologies of actin and PKC-θ were grouped into three categories: diffusive, focal, and annular. In a majority of the cells (80% of 51 cells) that were in contact with the native "bull's eye" pattern, actin appeared diffusive over the entire contact area (FIG. 2A). Other cells (20% of 51 cells) exhibited focal accumulation of actin, which colocalized with the anti-CD3 patch on the particle. However, cells that were in contact with the reverse "bull's eye" pattern only exhibited either annular (52% of 55 cells)

or diffusive (48% of 55 cells) morphology. Actin does not colocalize with fibronectin, but largely follows the anti-CD3 patterns on the particles.

Figure 2B:
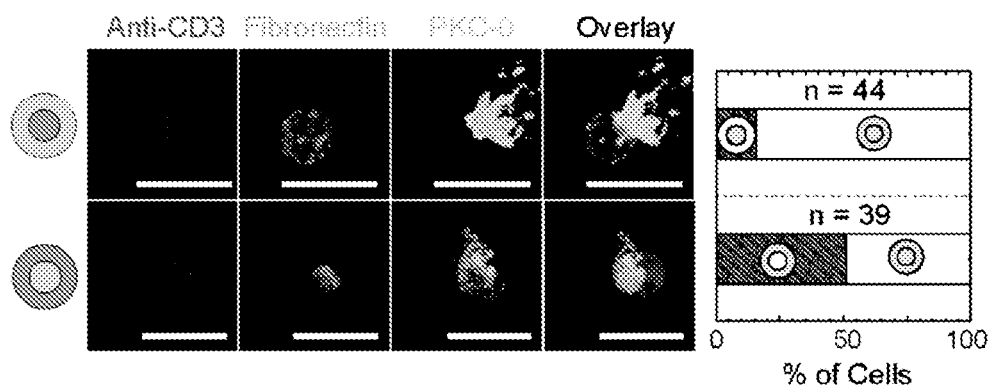
Figure 5:
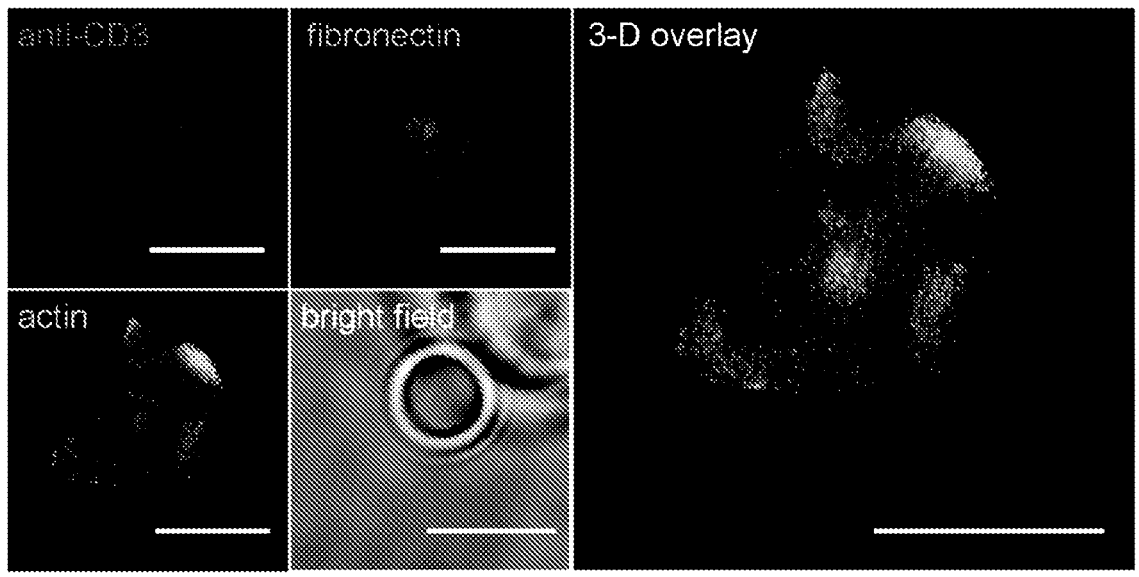
FIG. 5: 3-D fluorescence confocal images show intracellular clustering of actin in T cells stimulated by control particles that were uniformly coated with anti-CD3 and fibronectin. The images are representative of 36 cells. Scale bars: 5 µm.
Figure 6:
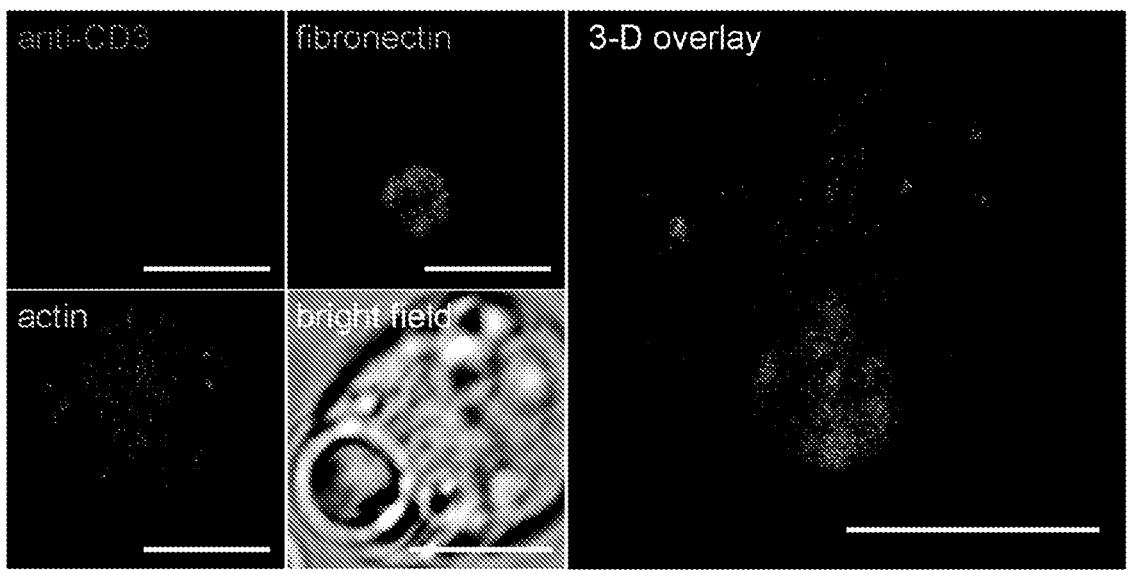
FIG. 6: 3-D fluorescence confocal images show intracellular clustering of PKC-θ in T cells stimulated by control particles that were uniformly coated with anti-CD3 and fibronectin. Scale bars: 5 µm.

Similar phenomena were observed for PKC-θ. Intracellular clustering of PKC-θ was either focal (16% of 44 cells) or diffusive (84% of 44 cells) in cells that were activated by the native "bull's eye" pattern (FIG. 2B). However, cells that were activated by the reverse "bull's eye" pattern exhibited only annular (51% of 39 cells) or diffusive (49% of 39 cells) accumulation of PKC-θ. To confirm that the intracellular clustering of actin and PKC-θ was indeed altered by the ligand patterns on particles, T cells were stimulated with particles that have uniform presentation of anti-CD3 and fibronectin. Only diffusive morphology of actin and PKC-θ was observed (FIGS. 5 and 6). It is evident that the intracellular clustering of the two key signaling proteins, actin and PKC-θ, is directed by the "bull's eye" protein patterns on particles.

The central accumulation of TCRs is known to lead to signaling termination. Prolonged T cell signaling has been observed when the T cell receptors were prevented from moving toward the center of the immunological synapse. The "bull's eye" patterns on particles described herein directed the clustering of two intracellular proteins: actin and PKC-0.

Figure 3A:
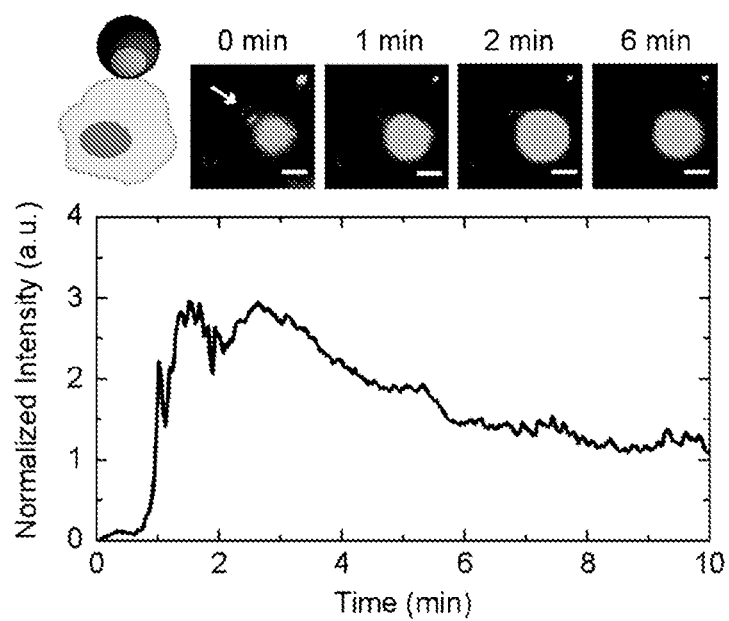
FIGS. 3A-3D: Data showing intracellular calcium elevation in T cells that were stimulated by the reverse (FIGS. 3A-3B) and the native (FIGS. 3C-3D) "bull's eye" Janus particles. Jurkat T cells were loaded with calcium-sensitive dye, Fluo-4 AM, whose fluorescence intensity increases with intracellular concentration of $Ca^{2+}$.

T cell activation was quantified by measuring intracellular $Ca^{2+}$ elevation. It is known that T cell activation leads to rapid entry of calcium ions into cytosol from both the endoplasmic reticulum (ER) and the extracellular solution. The amplitude and duration of the calcium elevation in T cells are directly related with the strength of T cell activation, with stronger stimuli giving more prominent and sustained calcium influx. Intracellular calcium elevation in single T cells was imaged by using the calcium-sensitive dye Fluo-4 acetoxymethyl ester (AM), whose fluorescence emission increases upon binding $Ca^{2+}$. As shown in FIG. 3A, when a Jurkat T cell made the initial contact with the reverse "bull's eye" pattern on a particle, a rapid increase of fluorescence intensity immediately followed, indicating a large influx of $Ca^{2+}$ into the cytosol. As T cell signaling proceeded, Fluo-4 fluorescence intensity gradually decreased. Plotting the fluorescence intensity (normalized to baseline) as a function of time showed the temporal changes of intracellular $[Ca^{2+}]$ during T cell activation. Calcium influx peaked within 2 minutes after the initial cell-particle contact, sustained for 1-3 minutes and gradually returned to a basal level. Such calcium influx is characteristic of normal T cell activation. In contrast, T cells that were stimulated by the native "bull's eye" particles exhibited transient calcium peaks of lower intensities (FIG. 3C). A delay between the initial cell-particle contact and the first calcium peak was also typical, indicative of a phase during which T cells searched for stimulatory signal from anti-CD3. The two cell-particle pairs are each representative of over 30 cells that were in contact with the "bull's eye" pattern.

Figure 3B:
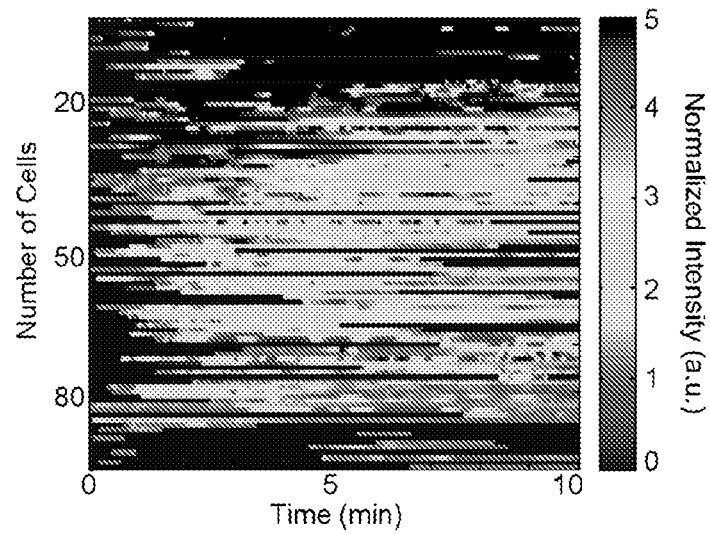
Figure 3C:
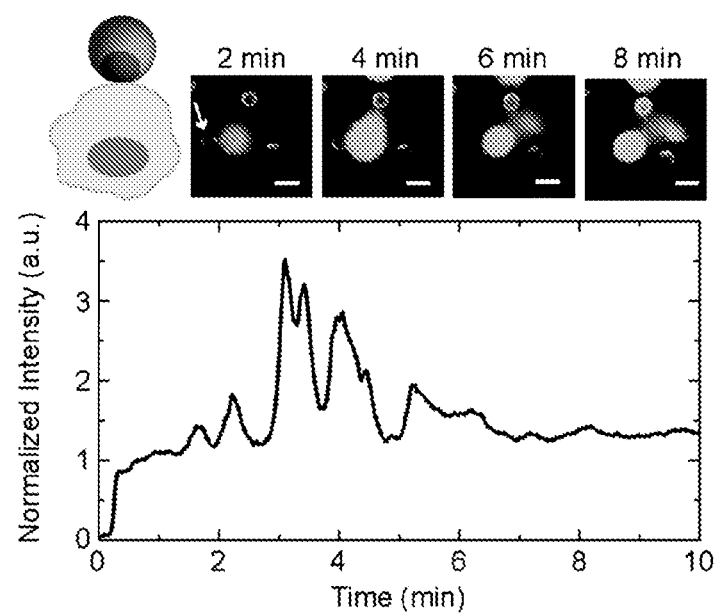
Figure 3D:
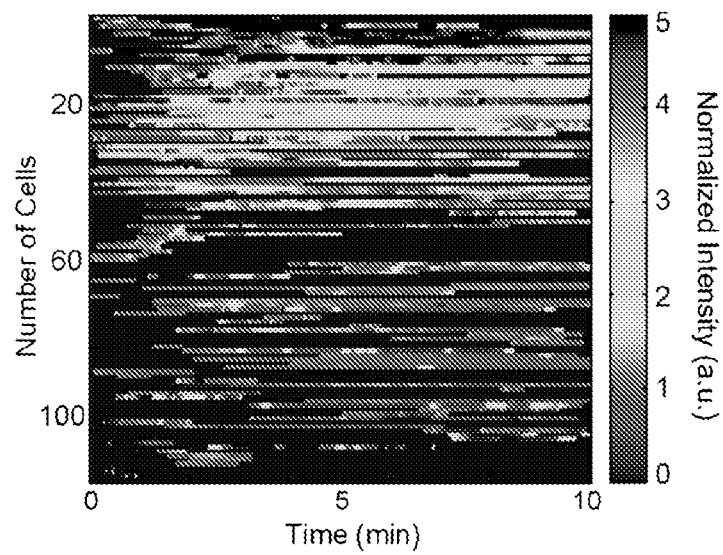
Figure 7:
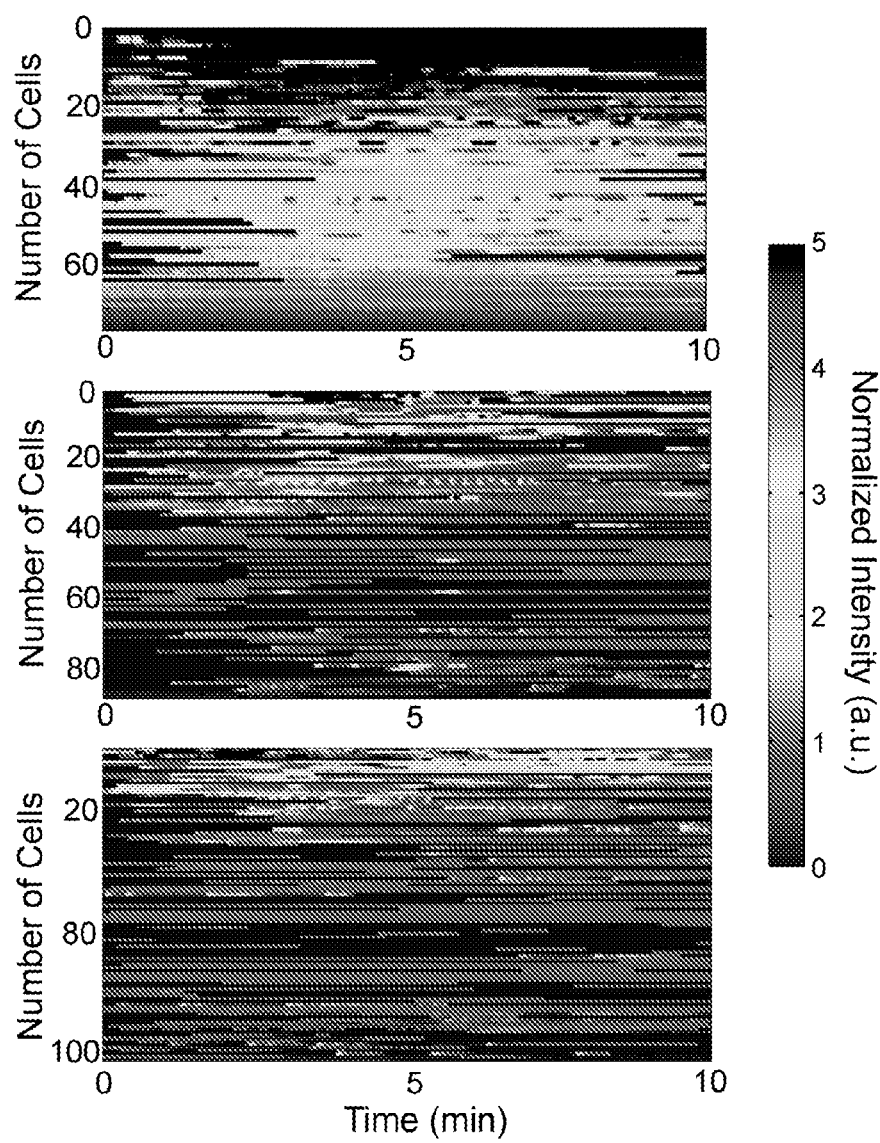
FIG. 7: Data showing intracellular calcium elevation in Jurkat T cells that were stimulated by particles coated with anti-CD3 (top panel), fibronectin (middle panel), and BSA (bottom panel). Ligand functionalization was uniform for all three control samples. Jurkat T cells were loaded with calcium-sensitive dye, Fluo-4, whose fluorescence intensity increases with intracellular $Ca^{2+}$ concentration. Normalized fluorescence intensities of individual cells are shown on a color scale. Time zero is defined as the time of each cell landing on the bottom of imaging chambers.

To further elucidate the global response of $Ca^{2+}$ signaling upon T cell stimulation by the "bull's eye" Janus particles, a large population of T cells was analyzed, and their normalized fluorescence intensities plotted as a function of time in heat maps (FIGS. 3B and 3D). Calcium elevation differed in T cells stimulated by the two types of particles—the reverse "bull's eye" Janus particles, in comparison to the native type—lead to more intense calcium influx in a larger fraction of cells. In control experiments in which particles were uniformly coated with anti-CD3, fibronectin, or BSA, it was confirmed that Jurkat T cells were activated by anti-CD3 but not by fibronectin alone (FIG. 7). The cell-to-cell variation of calcium signaling is characteristic of T cell activation and in agreement with previous reports. Given that the calcium heat maps were obtained from all particle-cell orientations, it is possible that the difference of calcium profiles is partially augmented by the different surface coverage of anti-CD3 on the two types of particles.

Both single-cell and bulk results confirmed that the spatial presentation of anti-CD3 and fibronectin on the particles influenced the strength and duration of calcium signaling during T cell activation. The stronger T cell activation by the reverse "bull's eye" particles agrees with the modulated annular localization of actin and PKC-θ, confirming that the "bull's eye" Janus particles modulate T cell activation by dictating the spatial organization of signaling proteins.

Using a microcontact printing method, micron-sized particles were generated as artificial antigen presenting cells that display "bull's eye" patterns of protein ligands on the particle surface. One pattern mimics the native organization of proteins in the immunological synapse, while the other is a reverse pattern of the same proteins ligands. It was found that the reverse "bull's eye" Janus particles lead to more intense and sustaining T cell calcium signaling than the native type. This is due to the differential T cell activation to the modulated intracellular localization of signaling proteins, which was confirmed for actin and PKC-θ. These results demonstrate that fixed arrangement of protein ligands on particle surfaces can be used to modulate T cell activation from outside in. This shows how multi-functional Janus particles can be designed as artificial antigen-presenting cells for fine-tuning T cell activation.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A biomimetic Janus particle comprising:
   a) a particle;
   b) at least one substantially concentric pattern of a first ligand population bound to the particle, wherein the first ligand population comprises one or more ligands involved in T cell activation and/or one or more molecules to which a ligand involved in T cell activation may be bound; and
   c) a second ligand population bound to the particle, wherein the second ligand population is different than the first ligand population and does not substantially overlap the substantially concentric pattern of the first ligand population, and wherein the second ligand population comprises one or more ligands involved in T cell activation and/or one or more molecules to which a ligand involved in T cell activation may be bound,
   wherein one of the first ligand population or second ligand population comprise an integrin-binding ligand.

2. The biomimetic Janus particle of claim 1, wherein the particle is a microparticle or a nanoparticle.

3. The biomimetic Janus particle of claim 2, wherein the particle is a silica particle, a polystyrene particle, a melamine resin particle, or a polymethacrylate particle.

4. The biomimetic Janus particle of claim 2, wherein the particle has a diameter within a range selected from the group consisting of: about 0.1 µm to about 20 µm; and about 0.5 µm to about 5 µm.

5. The biomimetic Janus particle of claim 1, wherein the particle is a silica particle having a diameter of about 3 µm.

6. The biomimetic Janus particle of claim 1, wherein the at least one substantially concentric pattern of the first ligand population has a diameter within a range selected from the group consisting of: about 10 nm to about 5 µm; and about 0.5 µm to about 3.5 µm.

7. The biomimetic Janus particle of claim 1, wherein the at least one substantially concentric pattern of a first ligand population has a diameter of about 1.7 µm.

8. The biomimetic Janus particle of claim 1, wherein the one or more ligands involved in T cell activation is selected from the group consisting of: anti-CD3 antibody; anti-CD28 antibody; anti-TCR antibody; an anti-CTLA4 antibody; and a ligand comprising a general integrin-binding motif, and wherein the one or more molecules to which a ligand involved in T cell activation may be bound is biotin.

9. The biomimetic Janus particle of claim 1, wherein the first ligand population comprises one or more ligands comprising a general integrin-binding motif and the second ligand population comprises one or more ligands capable of binding to at least one component of a T cell TCR complex.

10. The biomimetic Janus particle of claim 1, wherein the first ligand population comprises one or more ligands capable of binding to at least one component of a T cell TCR complex and the second ligand population comprises one or more ligands comprising a general integrin-binding motif.

11. The biomimetic Janus particle of claim 8, wherein the ligand comprising a general integrin-binding motif is selected from the group consisting of: fibronectin; collagen; laminin; vitronectin; fibrinogen; and thrombospondin.

12. The biomimetic Janus particle of claim 9, wherein the first ligand population comprises fibronectin and the second ligand population comprises an anti-CD3 antibody.

13. The biomimetic Janus particle of claim 9, wherein the first ligand population comprises fibronectin and the second ligand population comprises biotin.

14. The biomimetic Janus particle of claim 10, wherein the first ligand population comprises an anti-CD3 antibody and the second ligand population comprises fibronectin.

15. The biomimetic Janus particle of claim 10, wherein the first ligand population comprises biotin and the second ligand population comprises fibronectin.

16. The biomimetic Janus particle of claim 13, further comprising one or more streptavidin-conjugated ligands capable of binding to at least one component of a T cell TCR complex, wherein the one or more streptavidin-conjugated ligands is bound to the biotin.

17. The biomimetic Janus particle of claim 13, further comprising one or more biotinylated ligands capable of binding to at least one component of a T cell TCR complex, wherein the one or more biotinylated ligands is bound to the biotin via streptavidin.

18. The biomimetic Janus particle of claim 9, wherein the one or more ligands capable of binding to at least one component of a T cell TCR complex is selected from the group consisting of: anti-CD3 antibody; anti-CD28 antibody; anti-TCR antibody; and anti-CTLA4 antibody.

19. A composition comprising one or more Janus particles of claim 1.

20. A method of activating a population of T cells in vitro, comprising applying one or more biomimetic Janus particles of claim 1 to a population of T cells.

21. The method of claim 20, wherein the population of T cells comprises autologous T cells, isolated from a subject in need of an immunotherapy, heterologous T cells derived from a source other than the subject in need of an immunotherapy, or a combination thereof.

22. The method of claim 20, wherein the population of T cells comprises nave T cell, CD8$^+$ T cells, CD4$^+$ T cells, or a combination thereof.

23. The method of claim 20, wherein the population of T cells comprises antigen-specific T cells.

24. The method of claim 20, wherein the population of T cells comprises tumor antigen-specific T cells.

25. The method of claim 20, wherein the one or more biomimetic Janus particles are incubated with the population of T cells for about 5 minutes to about 2 week.

26. The method of claim 20, wherein the one or more biomimetic Janus particles are incubated with the population of T cells for about 1 hour to about 60 hours.

27. The method of claim 20, wherein the one or more biomimetic Janus particles are incubated with the population of T cells for about 24 hours to about 48 hours.

28. The method of claim 23, further comprising rinsing the population of T cells following incubation to remove the one or more biomimetic Janus particles.

29. A method of administering an immunotherapy to a subject in need thereof, the method comprising administering T cells activated according to the method of claim 20 to the subject.

30. The method of claim 29, wherein the immunotherapy is selected from the group consisting of: adoptive immunotherapy for cancer; tolerance induction in autoimmune disease; autologous immune enhancement therapy; and viral infection immunotherapy.

31. The method of claim 30, further comprising a step of preparative lymphodepletion in the subject prior to administering the activated T cells to the subject.

* * * * *